US012207966B2

(12) United States Patent
Maguire et al.

(10) Patent No.: US 12,207,966 B2
(45) Date of Patent: Jan. 28, 2025

(54) TUBE POSITION MONITORING SYSTEM (71) Applicant: COVIDIEN LP, Mansfield, MA (US)

(72) Inventors: Seamus P. Maguire, Athlone (IE);
Mark A. McGann, Ballybrittas (IE);
Kieran M. Donlon, Athlone (IE);
James P. Curley, Via Athlone (IE);
Daniel P. Waters, Ballinfull (IE);
Graham B. Fleming, Athlone (IE);
Sean Morris, Ballymurray (IE); Ronan J. Hanamy, Birr (IE); Noel Morgan, Athlone (IE); Rosemary Cahill, Ballymahon (IE); Conor Hand, Dublin (IE); Anne M. Savage, Athlone (IE); Izabela A. Ksienzyk, Athlone (IE)

(73) Assignee: COVIDIEN LP, Mansfield, MA (US)

(*) Notice: Subject to any disclaimer, the term of this patent is extended or adjusted under 35 U.S.C. 154(b) by 461 days.

(21) Appl. No.: 17/071,558

(22) Filed: Oct. 15, 2020

(65) Prior Publication Data
US 2021/0121155 A1 Apr. 29, 2021

Related U.S. Application Data (60) Provisional application No. 62/926,932, filed on Oct. 28, 2019.

(51) Int. Cl.
A61M 16/04 (2006.01)
A61B 1/00 (2006.01)
(Continued)

(52) U.S. Cl.
CPC ........ A61B 8/0841 (2013.01); A61B 1/00045 (2013.01); A61B 1/267 (2013.01);
(Continued)

(58) Field of Classification Search
CPC ..... A61B 8/0841; A61B 6/12; A61B 1/00045; A61B 1/267; A61M 16/04;
(Continued)

(56) References Cited

U.S. PATENT DOCUMENTS 5,622,169 A 4/1997 Golden et al.
6,161,537 A 12/2000 Gravenstein et al.
(Continued)

FOREIGN PATENT DOCUMENTS

EP 1863558 B1 * 1/2018 ......... A61B 18/1477

OTHER PUBLICATIONS

Lee, Hyung-Chul et al.; "Real-time endoscopic image orientation correction system using an accelerometer and gyrosensor," PLOS One, 12(11), Nov. 3, 2017, 12 pgs.

Primary Examiner — Colin T. Sakamoto
Assistant Examiner — Tommy T Ly (57) ABSTRACT A position monitoring system is provided that includes a tracheal tube having a distal portion with a radiopaque indicator. The tracheal tube is configured to be positioned within an airway of a patient. The position monitoring system also includes an external sensor configured to be positioned on an external surface of the patient. The external sensor includes an emitter configured to transmit energy into the patient and toward the distal portion and a detector configured to receive a reflected portion of the energy to permit identification of a position of the distal portion. The position monitoring system, in certain embodiments, further includes a video laryngoscope communicatively coupled to the external sensor. The video laryngoscope includes a display and a processor, and the processor is configured to instruct the display to present an indication of the position of the distal portion based on feedback from the detector.

13 Claims, 7 Drawing Sheets (51) Int. Cl.
*A61B 1/267* (2006.01)
*A61B 6/12* (2006.01)
*A61B 8/08* (2006.01)

(52) U.S. Cl.
CPC .............. *A61B 6/12* (2013.01); *A61M 16/04* (2013.01); *A61M 2205/32* (2013.01)

(58) Field of Classification Search
CPC .......... A61M 2205/32; A61M 16/0411; A61M 16/0688; A61M 16/0434; A61M 16/0683; A61M 2205/3317; A61M 2205/3375; A61M 2205/3553; A61M 2205/3561; A61M 2205/3592; A61M 2205/505; A61M 2205/581; A61M 2205/582; A61M 2205/584; A61M 2205/587; A61M 16/0488; A61M 2205/6054; A61M 2205/8206
See application file for complete search history.

(56) References Cited

U.S. PATENT DOCUMENTS

| | | | |
|---|---|---|---|
| 7,543,586 | B2 | 6/2009 | Qureshi et al. |
| 8,548,564 | B2* | 10/2013 | Peters ............... A61M 16/0486 |
| | | | 128/207.14 |
| 8,882,682 | B2 | 11/2014 | Qiu |
| 2006/0081255 | A1 | 4/2006 | Miller et al. |
| 2010/0145147 | A1 | 6/2010 | Pinsky et al. |
| 2010/0256482 | A1* | 10/2010 | Peters ............... A61M 16/0486 |
| | | | 600/424 |
| 2013/0025602 | A1* | 1/2013 | Hayman ........... A61M 16/0445 |
| | | | 128/207.15 |
| 2014/0275982 | A1* | 9/2014 | Hendrick .............. A61B 90/98 |
| | | | 606/130 |
| 2017/0189634 | A1* | 7/2017 | Larson .................. A61B 1/267 |
| 2017/0202543 | A1* | 7/2017 | Herdina ................. A61B 6/032 |
| 2018/0221610 | A1* | 8/2018 | Larson .................. H04N 7/183 |
| 2018/0235713 | A1* | 8/2018 | Krimsky ................ A61B 90/37 |
| 2019/0025040 | A1* | 1/2019 | Andreason ............ A61B 5/062 |
| 2020/0188640 | A1* | 6/2020 | Palushi ................... A61B 1/06 |
| 2021/0121651 | A1* | 4/2021 | Schaner .............. A61M 16/0411 |

* cited by examiner

TUBE POSITION MONITORING SYSTEM

CROSS-REFERENCE TO RELATED APPLICATIONS

The present application claims priority to and the benefit of U.S. Provisional Application No. 62/926,932, filed on Oct. 28, 2019, the disclosure of which is incorporated by reference in their entirety for all purposes.

BACKGROUND

The present disclosure relates generally to medical devices and, more particularly, to control systems and related methods for monitoring positions of tubes, such as airway or tracheal tubes, within patients.

This section is intended to introduce the reader to various aspects of art that may be related to the present disclosure, as described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, a patient may be intubated when an endotracheal tube is inserted through the patient's mouth or nose and further inserted into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. For example, during an intubation procedure, a practitioner may employ a video laryngoscope to facilitate introduction of the endotracheal tube. However, such visualization during introduction of the tube may not account for ongoing changes in the position of the tube within the trachea that may occur after introduction of the tube. For example, when a patient coughs, the tube may be dislodged from its desired location. Moreover, when a patient is jostled or moved within a care setting, the position or angle of the tube within the trachea may be changed.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a position monitoring system includes a tracheal tube comprising a distal portion having a radiopaque indicator, wherein the tracheal tube is configured to be positioned within an airway of a patient. The position monitoring system also includes an external sensor configured to be positioned on an external surface of the patient. The external sensor includes: an emitter configured to transmit energy into the neck of the patient and toward the distal portion; and a detector configured to receive a reflected portion of the energy to permit identification of a position of the distal portion. The position monitoring system further includes a video laryngoscope communicatively coupled to the external sensor. The video laryngoscope includes a display and a processor, and the processor is configured to instruct the display to present an indication of the position of the distal portion based on feedback from the detector.

In an embodiment, an external sensor configured to be positioned on an external surface of a neck of a patient includes a housing; an emitter coupled to the housing and configured to transmit energy into the neck of the patient; and a detector coupled to the housing. The detector is configured to receive a reflected portion of the energy and generate a signal indicative of a position of a radiopaque indicator of a tracheal tube within an airway of the patient. The external sensor also includes an output device coupled to the housing and configured to provide a first indication or a second indication based on the position of the distal end. The external sensor also includes a processor disposed within the housing and communicatively coupled to the emitter, the detector, and an output device of the external sensor. The processor is configured to: receive the signal from the detector; determine the position of the radiopaque indicator based on the signal; determine whether the position is within a threshold distance from the external sensor; and instruct the output device to output the first indication in response to determining that the position is within the threshold distance.

In an embodiment, a method is provided that includes the steps of receiving, at a video laryngoscope, communication that an external sensor is communicatively coupled; activating functionality associated with the external sensor based on the coupling of the external sensor; instructing, via a processor of the video laryngoscope, an emitter of an external sensor positioned on an external surface of a patient to transmit energy toward an airway of the patient; receiving, via the processor, a signal indicative of detection of a current position of a tracheal tube within the airway from a detector of the external sensor, wherein a distal portion of the tracheal tube comprises a radiopaque indicator that is detected by the detector; receiving, via the processor, a user input that the current position is a target position; communicating with an external sensor processor that the tracheal tube is in the target position to cause the external sensor processor to store the signal indicative of detection as the target position; and receiving a confirmation of the storing from the external sensor.

Features in one aspect or embodiment may be applied as features in any other aspect or embodiment, in any appropriate combination. For example, any one of system, laryngoscope, controller (e.g., processor-based controller), external sensor, or method features may be applied as any one or more other of system, laryngoscope, controller, external sensor, or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

A tracheal tube may be used to seal a patient's airway and provide positive pressure to the lungs when properly inserted into a patient's trachea. Positioning the tracheal tube at a desired position within the trachea during a tracheal intubation procedure and maintaining the desired position of the tracheal tube in the intubated patient may improve the performance of the tracheal tube and reduce clinical complications. In particular, the distal inserted end of the endotracheal tube may be positioned in the patient's trachea at a location substantially between the patient's vocal cords and carina. If an inflatable cuff of the tube is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal end of the tube, as well as maintenance of the proper placement of the tube while the patient is intubated, may result in improved ventilation to the patient.

Provided herein are position monitoring systems to facilitate positioning of a tracheal tube in a patient's airway, such as desired positioning relative to certain anatomical structures in and around the patient's airway and trachea. The positioning monitoring system includes an external sensor that is placed on or near the patient and that detects the tracheal tube position via one or more indicators on the tracheal tube, such as radiopaque markers of the tracheal tube. As disclosed herein, the external sensor generally includes an emitter that transmits energy (e.g., electromagnetic energy, sound energy) through the patient's neck to enter the airway and detects returned energy to identify or resolve a position of the tracheal tube within the airway. As such, the external sensor assists a practitioner in placing and identifying the position of the tracheal tube.

The external sensor may be a relatively inexpensive component of the monitoring system that may be placed on the patient at an accessible location (e.g., on the patient's neck) and that may function as an add-on or accessory device that is used during a laryngoscope-assisted intubation procedure to provide sensor data indicative tracheal tube position information, e.g., via output devices that provide visible, audible, or haptic feedback. Accordingly, in an embodiment, the external sensor may be capable of communicating with an available laryngoscope to provide position indicators on a display of the laryngoscope. In this manner, the caregiver receives the information related to the tracheal tube position as well as the image acquired by the camera without having to change a gaze direction during the intubation. Further, when a laryngoscope is not available, e.g., the intubation is performed without a laryngoscope or after the tracheal tube is inserted and the laryngoscope is removed, the inexpensive external sensor may further function as a standalone monitoring device that provides position monitoring feedback and such that the relatively more costly laryngoscope is freed for use in other patients. Accordingly, depending on the desired use case, the external sensor may be used to provide tracheal tube position information or feedback. In an embodiment, the tracheal tube position information may be provided via relatively simple output devices of the external sensor, such as on-board light sources that light red (malpositioned) or green (correctly positioned). In this manner, caregivers of varying skill levels may quickly assess tracheal tube position without the use of more complex devices such that the laryngoscope that involve skilled practitioners. The external sensor may operate with or without a coupled laryngoscope to provide position monitoring information during the intubation procedure and over the course of the intubation.

In an embodiment, the external sensor may facilitate maintaining a target position for the tracheal tube established by the caregiver performing the intubation. In one example, an anesthesiologist may provide an input to the tracheal tube position monitoring system when the tracheal tube is in the desired target position (e.g., based on experience and/or observing the video laryngoscope). The position monitoring system may associate the target position with characteristic sensor data acquired by the external sensor at the time the target position input is received. The system may subsequently monitor deviations from the characteristic sensor data via the external sensor to monitor whether the tracheal tube has moved outside of a threshold range from the target position.

In certain embodiments, the disclosed position monitoring systems and methods may be used in conjunction with any appropriate medical device, including, without limitation, a feeding tube, an endotracheal tube, an endobronchial tube, a tracheostomy tube, an introducer, an endoscope, a bougie, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor any suitable human patient, such as a trauma victim, an intubated patient, a patient with a tracheotomy, an anesthetized patient, a cardiac arrest victim, a patient suffering from airway obstruction, or a patient suffering from respiratory issues.

Figure 1:
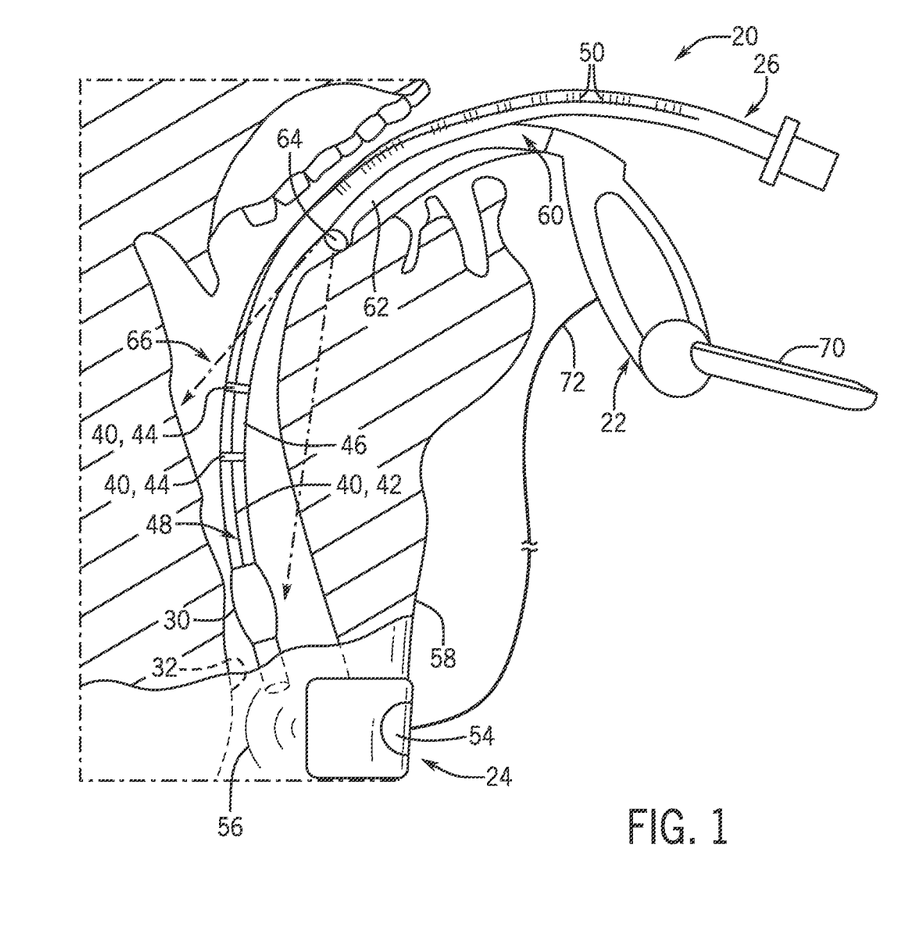
FIG. 1 is a schematic illustration of an implementation of a position monitoring system including a video laryngoscope and an external sensor to facilitate tracheal tube placement, in accordance with certain embodiments of the disclosure.

FIG. 1 shows an embodiment of a position monitoring system 20 including a laryngoscope, depicted as a video laryngoscope 22, an external sensor 24, and a tracheal tube 26. The tracheal tube 26 is presently illustrated as an endotracheal tube, which has an inflatable balloon cuff 30 that may be inflated to form a seal against tracheal walls 32 of a patient's trachea. However, it should be understood that the position monitoring system 20 may be used in conjunction with other types of tracheal tubes as provided herein. Further, the tracheal tubes may be cuffed or uncuffed. Notably, the tracheal tube 26 also includes one or more radiopaque markers 40 or indicators that permit the external sensor 24 to resolve a position of the tracheal tube 26 within the trachea. In the depicted embodiment, the radiopaque markers 40 include a longitudinal line 42 that is disposed along a length of the tracheal tube 26, as well as two circumferential lines 44 disposed around an outer surface 46 of the tracheal tube 26.

The radiopaque marker or markers 40 may be formed from or may include one or more materials that are distinguishable by the external sensor 24 from the materials forming the main body 48 of the tracheal tube 26 and that permit the external sensor 24 to sense the position of the tracheal tube 26. For example, the radiopaque markers 40 may include a relatively opaque material, a relatively dense material (e.g., denser than cartilage), a radio-frequency identification (RFID) tag, and so forth. In an embodiment, the radiopaque markers 40 may be formed from a less pure version (e.g., including one or more impurities) or a less transparent of the material of the main body 48. The radiopaque markers 40 may be printed on the outer surface of the tracheal tube 26 or may be co-extruded with the main body 48 during manufacturing. As illustrated, the tracheal tube 26 also includes depth markers 50 that provide a numerical visualization of the depth of the tracheal tube 26 within the trachea. By including both the depth markers 50 and the radiopaque markers 40, the tracheal tube 26 provides redundancy to the intubation procedure that improves consistency, such as by facilitating visual verification of electronic determinations and outputs of the position monitoring system 20.

As recognized herein, the video laryngoscope 22 and the external sensor 24 may coordinate to facilitate initial placement of the tracheal tube 26 within the trachea. Further, the position monitoring system 20 may be used to monitor the position of the tracheal tube 26 over any desired time interval, with or without the presence of the video laryngoscope 22. The external sensor 24 includes an emitter 54 (e.g., electromagnetic emitter, ultrasound emitter) that directs energy 56 through an external surface 58 of a neck of the patient. The radiopaque markers 40 interact with the energy 56 in a manner to permit the position monitoring system 20 to pinpoint or resolve a position of the tracheal tube 26. In some embodiments, the emitter 54 is implemented as a transducer that includes a detector that permits resolution of the position of the tracheal tube 26, though as discussed below, a separate, dedicated detector component may be alternatively included within the external sensor 24. Moreover, although primarily discussed herein as being electromagnetic energy or waves, it should be understood that the energy 56 provided by the emitter 54 may be any suitable energy or signal that permits resolution of the position of the tracheal tube 26, including sound waves that are generated by an ultrasound device.

With reference now to the video laryngoscope 22, the illustrated embodiment of the video laryngoscope 22 includes a blade 60 and a camera stick 62 supporting a laryngoscope camera 64. During a laryngoscopy, the blade 60 is inserted into the airway and positioned to view an upper portion 66 of the airway. The laryngoscope camera 64 thereby transmits image data to a display 70 of the video laryngoscope 22, which presents the image data to a practitioner to facilitate efficient advancement of the tracheal tube 26 to a target position within the trachea. The video laryngoscope 22 is illustrated as having a wired connection 72 to the external sensor 24 in the present embodiment. In other embodiments, the external sensor 24 and the video laryngoscope 22 may be communicatively coupled via a wireless connection. The video laryngoscope 22 may coordinate operation of the display 70 to display one or more indicators based on data acquired by the external sensor 24 to provide guidance and verification of the placement of the tracheal tube 26 within the airway, as described in more detail below.

Figure 2:
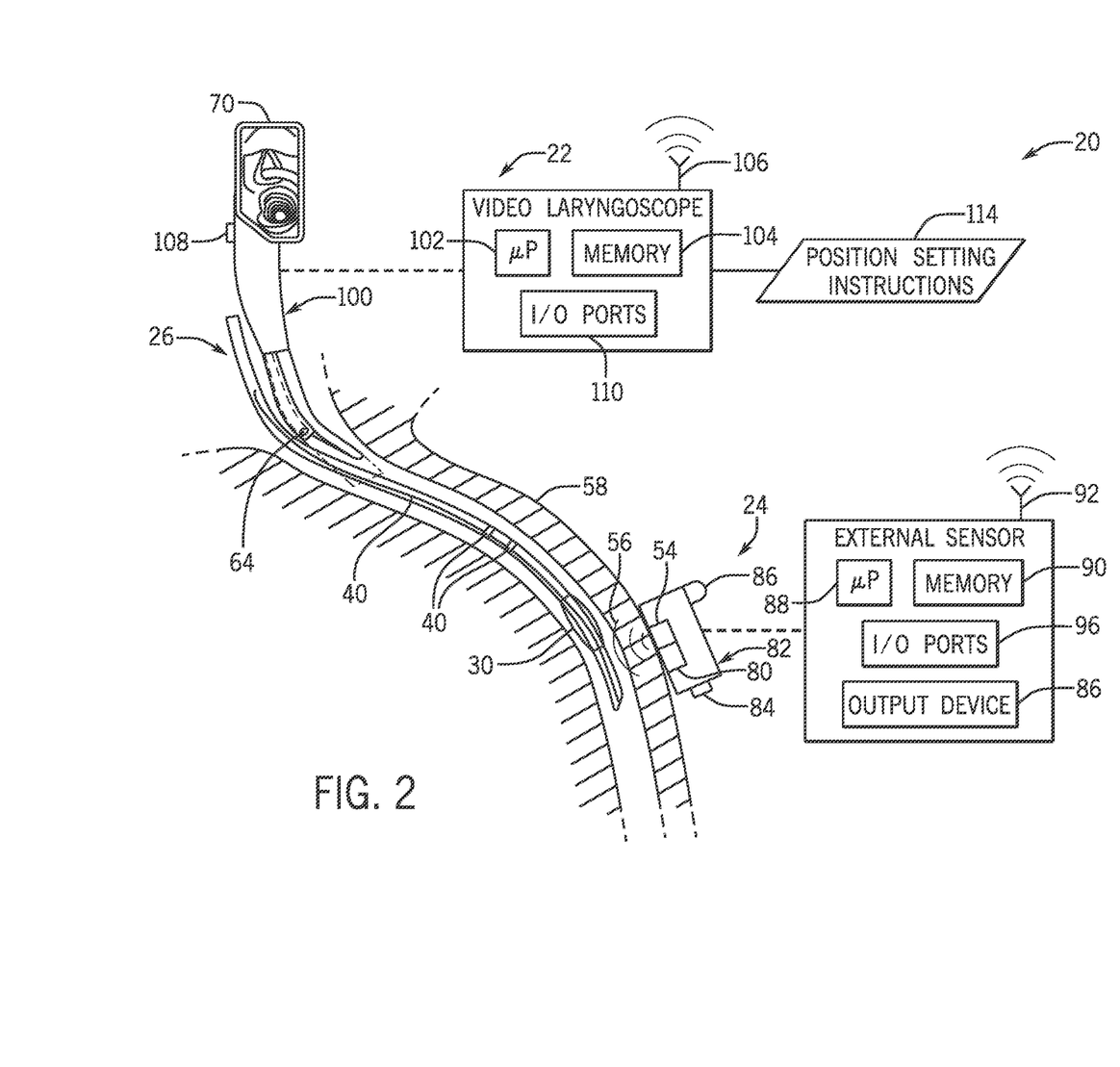
FIG. 2 is a block diagram of components of the position monitoring system of FIG. 1, in accordance with certain embodiments of the disclosure.

FIG. 2 is a schematic diagram of the position monitoring system of FIG. 1 showing an embodiment in which the video laryngoscope 22 and the external sensor 24 operate in conjunction to provide identification information indicative of a location of the tracheal tube 26, which includes the radiopaque marker/s 40 and the balloon cuff 30. As disclosed, the external sensor 24 includes the emitter 54 that transmits energy 56 into the external surface 58 of the patient. The external sensor 24 of the depicted embodiment also includes a detector 80 that receives a reflected portion of the energy 56 returned from the patient. As recognized herein, the emitter 54 may transmit energy 56 into the patient that permits the detector 80 to generate detector data based on the position of the radiopaque marker/s 40 or other indicators of the tracheal tube 26 relative to the external sensor 24, which is generally fixed in position on the patient's skin. The detector data is used to determine the location of the tracheal tube 26 or identify movement of the tracheal tube 26. For example, the emitter 40 may output sound energy, electromagnetic energy such as gamma radiation or x-rays, or an electromagnetic field that reads an RFID tag of the tracheal tube 26 that is detected by the detector 80.

In the illustrated embodiment, the emitter 54 and the detector 80 are coupled to (e.g., disposed on or within) a housing 82 of the external sensor 24. The external sensor 24 also includes a user-selectable button 84 and on-board output devices 86, depicted here as a light indicator, such as a light-emitting diode (LED). The output device 86 may, alternatively or additionally, include a speaker, a display, and/or a haptic element. Moreover, the external sensor 24 includes other suitable control circuitry and hardware within or coupled to the housing 82, such as a processor 88 (e.g., sensor processor), a hardware memory 90, communications circuitry 92, and input/output ports 96.

Respectively coupled to a laryngoscope handle 100, the video laryngoscope 22 also includes a processor 102 (e.g., primary processor), a hardware memory 104, communications circuitry 106, a user-selectable button 108, and input/output ports 110. The practitioner may provide inputs to the video laryngoscope 22 via the user-selectable button 108 or a sensor (e.g., a capacitive touch screen sensor on the display 70, or other mechanical or capacitive buttons or keys on the case 100) to convey user inputs that are provided to the processor 102, thereby facilitating detection and positioning of the tracheal tube 26. In certain embodiments, additional user input devices are provided, including one or more switches, toggles, or soft keys. The video laryngoscope 22 and the external sensor 24 may also each include a respective power source (e.g., an integral or removable battery) that provides power to components therein.

In some embodiments, the communications circuitry 92, 106 of one or both of the external sensor 24 and the video laryngoscope 22 may include a transceiver that facilitates handshake communications with mobile devices, remote medical devices, and full-screen monitors, which may each provide input to or receive information from the position monitoring system 20. The communications circuitry 92, 106 may provide collected data, such as received images or locations of the tracheal tube 26, to additional monitors in real time via any suitable communication protocol, including WI-FI® or BLUETOOTH®. Moreover, the input/output ports 96, 110 permit the video laryngoscope 22 and the external sensor 24 to be physically coupled to any other suitable devices, including each other. In some embodiments, the external sensor 24 may operate as an independent scanning device that leverages the emitter 54 and/or the detector 80 to identify positions of the vocal cords and carina within the patient, then transmits information indicative of the positions to the video laryngoscope 22 or another display device that is connected through the input/output port 96 or the communications circuitry 92.

The processors 88, 102 may include one or more application specific integrated circuits (ASICs), one or more general purpose processors, one or more controllers, one or more programmable circuits, or any combination thereof. For example, the processor 102 of the video laryngoscope 22 may also include or refer to control circuitry for the display 70. The memories 90, 104 may include volatile memory, such as random access memory (RAM), and/or non-volatile memory, such as read-only memory (ROM). In one embodiment, the received signal from the laryngoscope camera 64, e.g., image data comprising one or more images, may be processed, enhanced, resized, etc., according to stored instructions executed by the processor 102. Further, the image data may be displayed with overlaid indicators or markings to facilitate tube positioning based on feedback from the external sensor 24, as discussed below. The image data may be stored in the memory 104, and/or may be directly provided to the processor 102. Further, the image data and positioning data for each patient intubation may be stored and collected for later review or reference.

The memories 90, 104 also include stored instructions, code, logic, and/or algorithms that may be read and executed by the respective processor 88, 102 to perform the techniques disclosed herein. Additionally, the present embodiment of the memory 104 of the video laryngoscope 22 includes a set of positioning setting instructions 114 that correlates patient characteristics with positioning depths. For example, the positioning setting instructions 114 may provide a target tube depth or target external sensor 24 placement for multiple patient characteristics, including various ranges of age, height, weight, and so forth for particular patients. The external sensor 24 of certain embodiments may also store tracking information in the memory 90, thus facilitating collection and analysis of the positions of the tracheal tube 26 within the patient over time.

Figure 3:
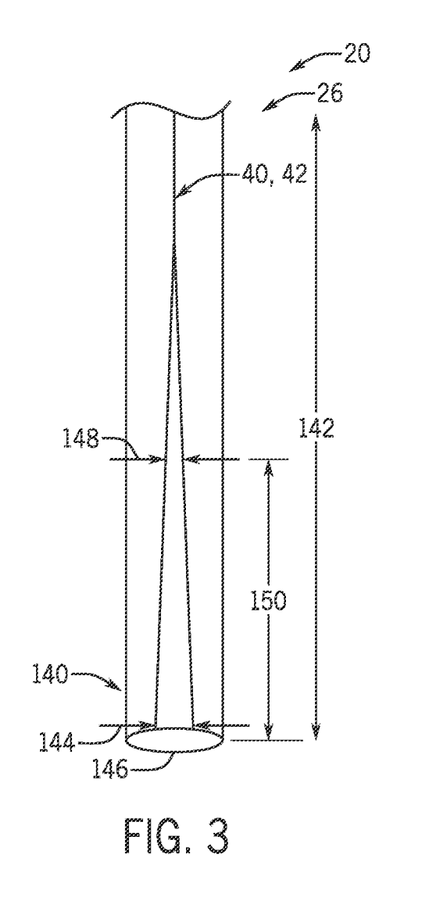
FIG. 3 is a schematic diagram of a tip of a tracheal tube including a shaped radiopaque marker that may be used in conjunction with the position monitoring system, in accordance with certain embodiments of the disclosure.

The tracheal tube 26 may have any suitable arrangement of the radiopaque markers 40 that are discernable to the external sensor 24. For example, FIG. 3 is a schematic diagram of a distal portion 140 of the tracheal tube 26 having an embodiment of the longitudinal line 42 that is shaped, e.g., tapered, along a longitudinal axis 142 of the tracheal tube 26. In particular, the longitudinal line 42 has a first width 144 at a distal tip 146 of the tracheal tube 26 that is larger than a second width 148 of the longitudinal line 42 spaced from the distal tip 146 by a distance 150. By providing a larger surface area or volume of radiopaque material at the distal portion 140 of the tracheal tube 26, the position monitoring system 20 may more efficiently identify the position of the tracheal tube 26 within the patient's trachea, with a reduced amount of radiopaque material compared to tracheal tubes that have a constant-width line of radiopaque material along their entire length. For example, the differences in an intensity of the detector signal generated by the detector 80 in response to the first width 144 relative to the second width 148 may permit resolution of the position of the distal tip 146 relative to the detector 80. Accordingly, the processor 88, 102 may be configured to identify a characteristic detector signal that changes in intensity in relation to movement of the distal tip 146 past the detector 80.

Figure 4:
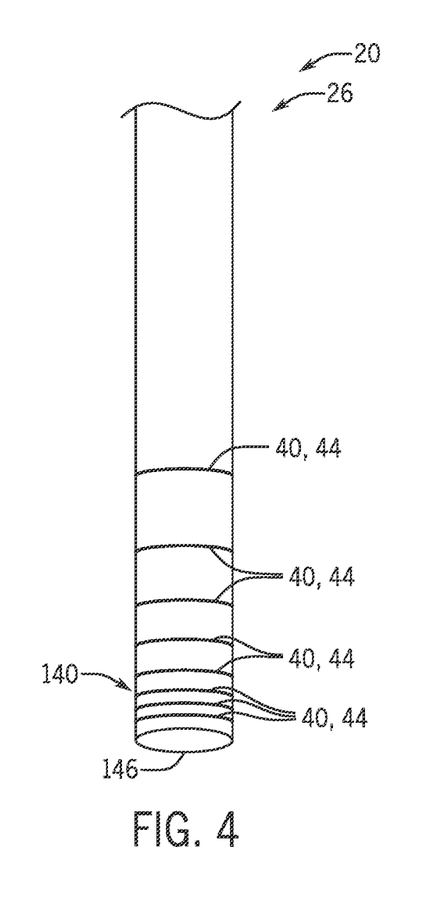
FIG. 4 is a schematic diagram of a tip of a tracheal tube including circumferential radiopaque markers that may be used in conjunction with the position monitoring system, in accordance with certain embodiments of the disclosure.

Moreover, FIG. 4 is a schematic diagram of the distal portion 140 of the tracheal tube 26 including circumferential lines 44 that are spaced closer together at the distal tip 146 of the tracheal tube 26. In other words, the circumferential lines 44 are denser proximate to the distal tip 146 of the tracheal tube 26, progressing to less dense further from the distal tip 146. The illustrated embodiment of the tracheal tube 26 therefore provides similar benefits to detection and material use as the tracheal tube 26 of FIG. 3. However, it should be understood that the disclosed techniques may be used in conjunction with a conventional tracheal tube 26 having a generally constant width radiopaque longitudinal line 42. The processor 88, 102 may be configured to operate during an intubation procedure to track movement of the distal tip 146 towards the detector 80, e.g., via a change in intensity of the detected signal. A point where the detected signal transitions to a relatively constant signal (e.g., a change in intensity decreases) may be indicative of the distal tip 146 being positioned in range of the external sensor 24.

Figure 5:
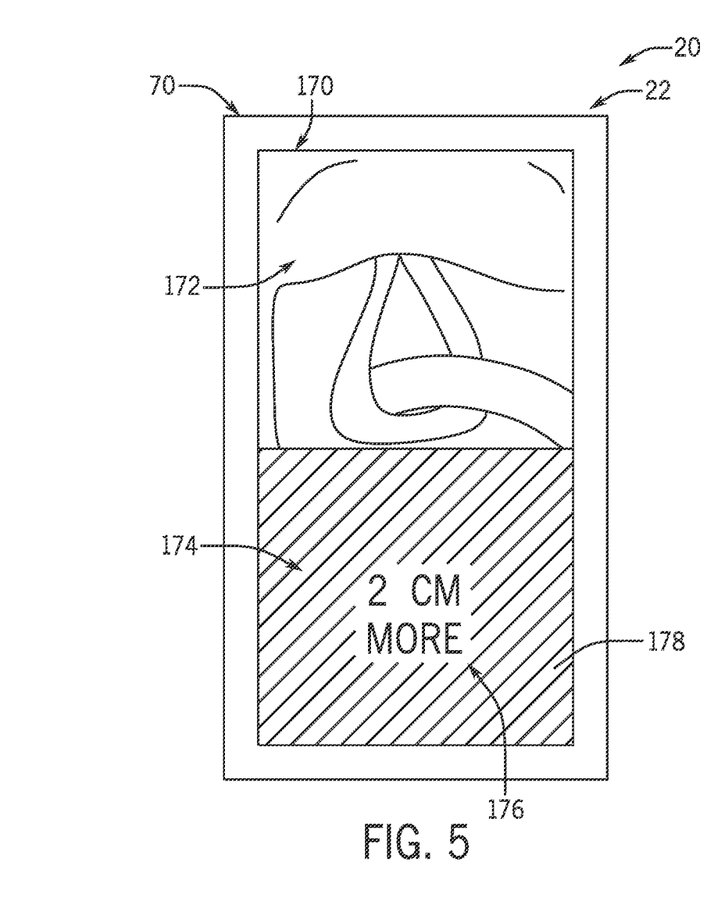
FIG. 5 is a schematic illustration of a user interface for a video laryngoscope of the position monitoring system that includes position indicators, in accordance with certain embodiments of the disclosure.

FIG. 5 is a schematic illustration of a user interface 170 included on the display 70 of the video laryngoscope 22 to provide indications of user instructions for appropriately positioning the tracheal tube 26. In the present embodiment, the user interface 170 is partitioned into a video portion 172 that relays the image data captured by the laryngoscope camera 64 and an instructional portion 174 that provides instructions relating to a movement of the tracheal tube 26 to reach a target position. In some embodiments, the entire display 70 initially presents the image data captured by the laryngoscope camera 64 within a full pane of the display 70. Then, in response to determining that the external sensor 24 has been communicatively coupled to the video laryngoscope 22 or powered on, the display 70 may transition to present the instructional portion 174 in conjunction with the video portion 172. As recognized herein and discussed in more detail below, the position monitoring system 20 may determine a target position for the tracheal tube 26 as a position within a threshold distance of the external sensor 24 or at a target depth within the airway. As such, the instructional portion 174 may present a movement parameter 176 that indicates a determined distance between a current position of the tracheal tube 26 and the target position.

In some embodiments, the instructional portion 174 may also include a background color 178 or pattern that indicates desired positioning of the tracheal tube 26. For example, the display 70 of the video laryngoscope 22 may present a red background in the instructional portion 174 when the tracheal tube 26 is beyond a first threshold distance from the target position. Then, in response to determining that the tracheal tube 26 is within the first threshold distance but outside a smaller, second threshold distance from the target position, the display 70 may present a yellow background in the instructional portion 174. Moreover, in response to determining that the tracheal tube 26 is within the second threshold distance from the target position, the display 70 may include a green background in the instructional portion 174. It should be understood that the range-based colored backgrounds discussed herein are examples of the multiple user-configurable settings that may be included on the display 70 of the video laryngoscope 22, or alternatively, on a similar display of the external sensor 24.

Figure 6:
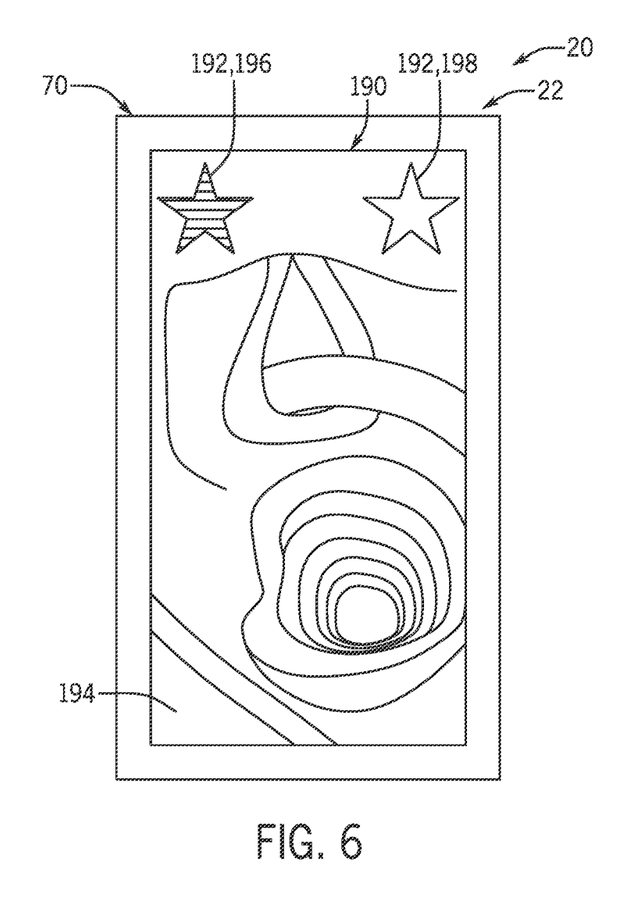
FIG. 6 is a schematic illustration of a user interface for a video laryngoscope of the position monitoring system that includes position indicators, in accordance with certain embodiments of the disclosure.

FIG. 6 is a schematic illustration of a user interface 190 for the display 70 of the video laryngoscope 22 that includes generated representations to provide feedback regarding positioning of the tracheal tube 26. In particular, the user interface 190 of the display 70 may include virtual objects 192 overlaid on image data 194 captured by the laryngoscope camera 64 to indicate various statuses related to the intubation procedure. For example, an outlined star item 196 may be displayed that has a fill corresponding to the colors discussed above. Alternatively or additionally, a filled star item 198 may be displayed over the image data 194 in response to the position monitoring system 20 determining that the tracheal tube 26 is within a predetermined threshold distance from the target position. In other embodiments, any suitable virtual objects may be overlaid on image data or otherwise presented on the display 70 or a display of the external sensor 24 to appropriately tune placement of the tracheal tube 26.

Figure 7:
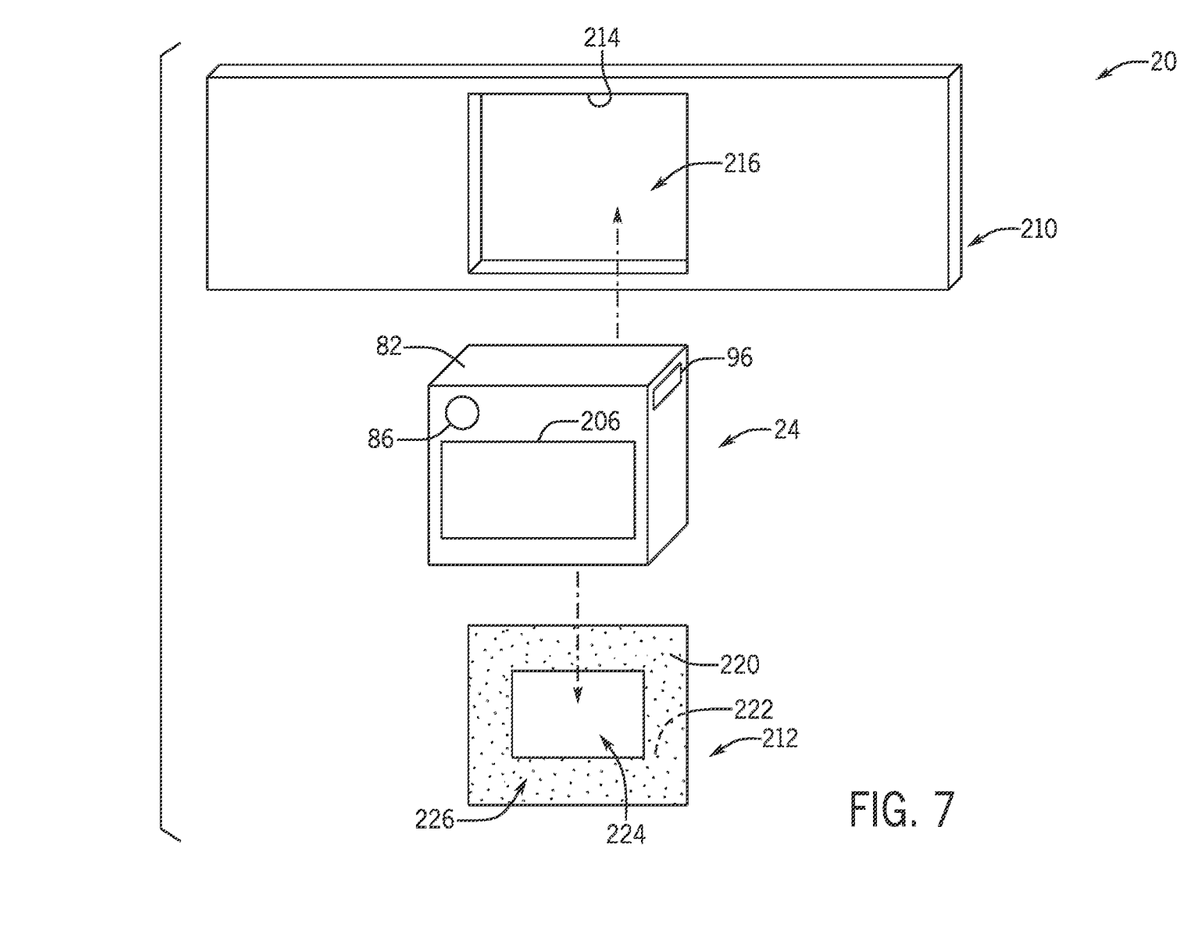
FIG. 7 is a schematic illustration of the external sensor of the position monitoring system, in accordance with certain embodiments of the disclosure.

FIG. 7 is a schematic illustration of the external sensor 24, which includes the output device 86, the input/output port 96, and a display 206. Moreover, the external sensor 24 may be provided on the patient via a strap 210 and/or an adhesive sticker 212. To facilitate retention of the external sensor 24 to the patient, the strap 210 may be formed of any suitable material and be designed to have a closure and an adjustable length that corresponds to a circumference of the patient's neck. In an embodiment, the strap 210 includes a cradle 214 that define a receptacle 216 or harness, which is designed to reversibly receive and couple to the housing 82 of the external sensor 24. In other embodiments, the strap 210 may be permanently coupled to or integrally formed with the housing 82, such as in embodiments in which the housing 82 and the strap 210 are injection molded and/or formed of plastic. In some embodiments, the strap 210 and/or the housing 82 of the external sensors 24 are reusable. In other embodiments, the strap 210 and/or the housing 82 are single use or patient-specific components that are discarded or cleaned after use. The position monitoring system 20 implementing any of these embodiments therefore reduces cross-contamination between patients, while facilitating the internal components of the external sensor 24 to be efficiently reused.

In other embodiments, the external sensor 24 of the present embodiment may instead be coupled to the sticker 212 that has an adhesive disposed on both a front surface 220 and a reverse surface 222 of the sticker 212. The adhesive may therefore retain the external sensor 24 to the sticker 212 and retain the sticker 212 against the external surface 58 of the patient during initial intubation or tube position monitoring. As illustrated, an opening 224 is defined within a main body 226 of the sticker 212 to permit the emitter 54 and the detector 80 to directly contact the external surface 58 of the patient. In other embodiments, the sticker 212 may include a translucent insert in place of the opening 224 that permits the emitter 54 and the detector 80 to provide and receive signals through the translucent insert.

In an embodiment, the external sensor 24 implemented with the sticker 212 may be a single-use component that is discarded after use, rather than being cleaned or sterilized for use on another patient. In other embodiments, the sticker 212 is disposable and the housing 82 of the external sensor 24 is sterilized for subsequent uses. It should be understood that various components of the position monitoring system 20 may be designed as reusable or disposable to suit a wide variety of patient applications. Additionally, the receptacle 216 of the strap 210 or the opening 224 of the sticker 212 may be omitted in certain embodiments in which the emitter 54 and the detector 80 cooperate to detect the radiopaque markers 40 through material of the strap 210 or the sticker 212.

Figure 8:
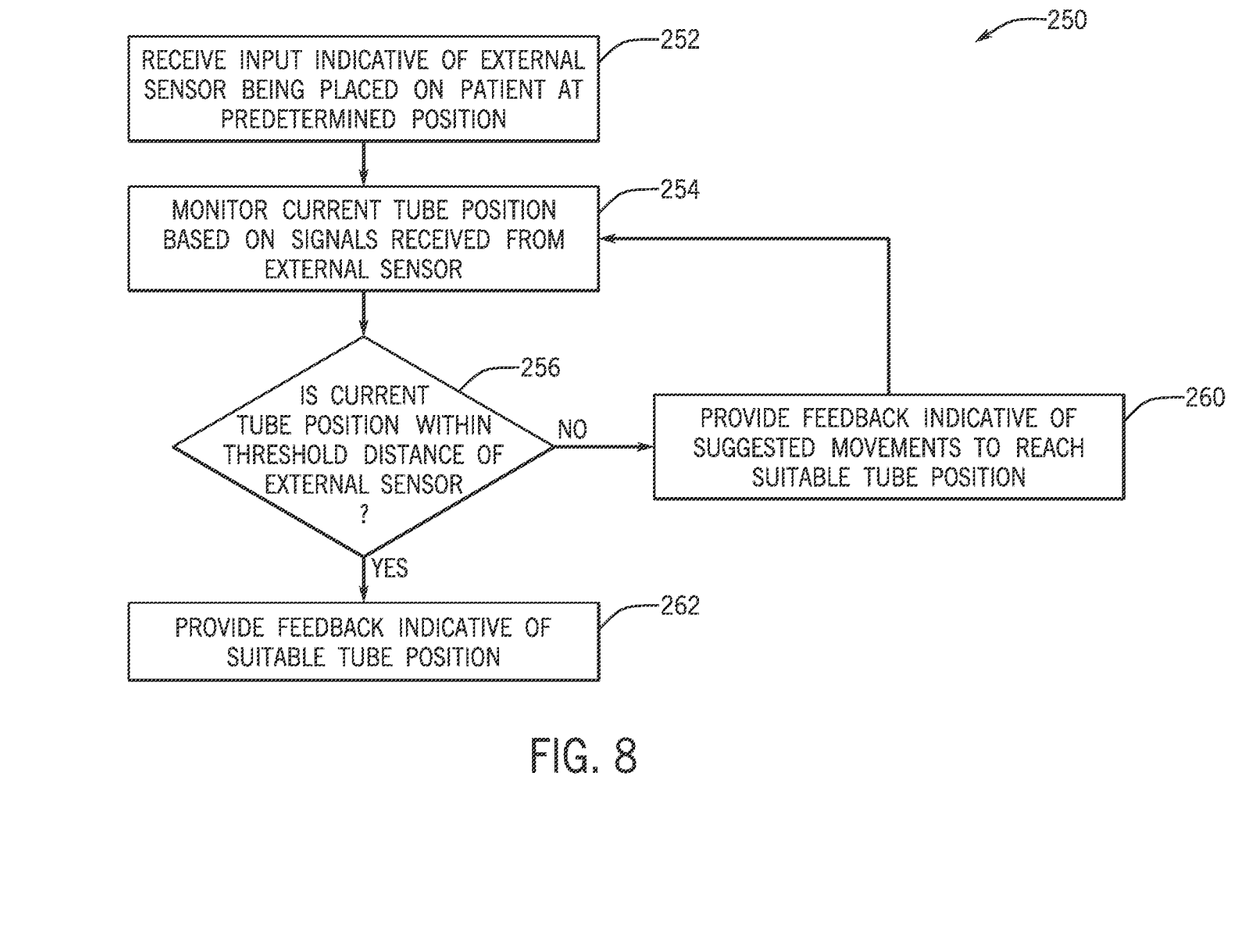
FIG. 8 is a flow diagram of a method of operating a video laryngoscope of the position monitoring system during an intubation procedure, in accordance with certain embodiments of the present disclosure.

With the above understanding of the components of the position monitoring system 20 in mind, further discussion is provided herein regarding processes of operating example embodiments of the position monitoring system 20. For example, FIG. 8 is a flow diagram of a method 250 of intubating a patient via the position monitoring system 20, in accordance with some embodiments. The method is generally indicated by reference number 250 and includes various steps or actions represented by blocks. It should be noted that the method 250 may be performed as an automated procedure by a system, such as the position monitoring system 20. Further, certain steps or portions of the method 250 may be performed by separate devices. For example, in some embodiments, a first portion of the method 250 may be performed by the video laryngoscope 22, while a second portion of the method 250 may be performed by the external sensor 24. In some embodiments, portions of the method 250 may be performed continuously or intermittently for long-term patient monitoring or at any appropriate interval depending on the particular situation of the intubated patient. Further, the steps of method 250 may be performed during insertion of the tracheal tube 26 into the patient.

In the illustrated embodiment, the method 250 begins with the video laryngoscope 22 receiving input indicative of the external sensor 24 being placed, at step 252, on the patient at a predetermined position, such as a position between the vocal chords and the carina of the patient. Generally, the external sensor 24 is secured to the external surface 58 of the patient at the predetermined position that corresponds to a target depth at which the tracheal tube 26 is to be disposed. The input may be indicative of the external sensor 24 being available for communicative coupling, such as via wired coupling to the I/O port 110 of the video laryngoscope 22 or via wireless pairing. In embodiments in which the video laryngoscope 22 stores the position setting instructions 114, the display 70 of the video laryngoscope 22 may indicate a position on the patient at which the external sensor 24 is recommended to be placed. For example, the video laryngoscope 22 may determine from user input, or otherwise retrieve, a height and age of the patient and recommend that based on the height and age, the external sensor 24 should be placed 10 centimeters (cm) below a jaw line of the patient. Such instructions may facilitate efficient intubation of the patient, as will be understood. After placing the external sensor 24, the practitioner may actuate the user-selectable button 84 on the external sensor 24 or the user-selectable button 108 on the video laryngoscope 22 to indicate to the position monitoring system 20 that the external sensor 24 is placed, in some embodiments, thereby initiating subsequent portions of the method 250.

With the external sensor 24 placed and secured in the predetermined position, at step 254, the video laryngoscope 22 may monitor a current position of the tracheal tube 26 based on signals that the video laryngoscope 22 receives from the external sensor 24. As mentioned, the emitter 54 of the external sensor 24 transmits the energy 56 into the airway of the patient, and the detector 80 generates signals based on the transmitted energy 56 that permit determination of the current position of the tracheal tube 26. The emitter 54 may transmit the energy 56 continuously, at predetermined intervals, or in any other suitable pattern that permits the tracheal tube 26 to be detected by the detector 80. In situations in which the detector 80 does not detect the tracheal tube 26, the external sensor 24 may determine that the tracheal tube has been misdirected to the esophagus and provide an alert indicative of the incorrect intubation.

In some embodiments, the external sensor 24 determines a distance between the tracheal tube 26 and the external sensor 24 and transmits signals indicative of the distance to the video laryngoscope 22. In other embodiments, the external sensor 24 passes unprocessed data from the detector 80 to the video laryngoscope 22, which determines a position parameter indicative of the position of the tracheal tube 26. For example, the parameter may be the distance between the tracheal tube 26 and the external sensor 24. By processing the data from the detector 80 at the video laryngoscope 22, the position monitoring system 20 of certain embodiments permits the external sensor 24 to be efficiently constructed with less complicated components, which are suitable for embodiments in which the external sensor 24 is single-use. Further, the video laryngoscope 22 may be programmed to operate in a specialized mode to activate the additional functionality (e.g., position information display) associated with the external sensor 24 when the external sensor 24 is available. However, when the external sensor 24 is unavailable, the video laryngoscope 22 may operate in a conventional manner.

In either case, based on the current position of the tracheal tube 26, the video laryngoscope 22 determines, at step 256, whether the current position is within a threshold of the determined position parameter, e.g., the threshold distance of the external sensor 24. For example, the video laryngoscope 22 may store the threshold distance as a static, predetermined parameter that is utilized to determine whether the tracheal tube 26 is positioned substantially even or level with the external sensor 24. In some embodiments, the threshold distance is set as 1 centimeters (cm), 3 cm, 5 cm, and so forth. It should be understood that in other embodiments, the video laryngoscope 22 may individually select the threshold distance based on the respective anatomical characteristics of the patient, such that patients who are estimated to have a larger distance between their airway and the external surface 58 of the neck are intubated with reference to a larger value as the threshold distance.

In response to determining that the current position of the tracheal tube 26 is not within the threshold distance of the external sensor 24, the video laryngoscope 22 provides, at step 260, feedback indicative of suggested movements to move the tracheal tube 26 to a suitable tube position. For example, as discussed above, the display 70 of the video laryngoscope 22 may indicate, via the instructional portion 174 of the user interface 170, that the tracheal tube 26 should be moved 2 cm deeper within the airway to reach a target or suitable position. It should be understood that the display 70 may additionally provide feedback regarding situations in which the tracheal tube 26 is disposed beyond a suitable position, and that in such embodiments, the display 70 may indicate a target amount that the tracheal tube 26 should be moved out of the airway. The video laryngoscope 22 may continuously update the instructions provided to the practitioner as the position of the tracheal tube 26 is tuned, such that a progressively smaller suggested movements are recommended to dispose the tracheal tube 26 in the suitable position. In other embodiments, the external sensor 24 may include the display 206 to indicate the suggested movements of the tracheal tube 26 and/or illuminate a light indicator of the output device 86 to coordinate with the suggested movements or movement parameter 176 (e.g., red for outside a first threshold, yellow for within the first and outside a second threshold, green for within the second threshold).

Alternatively, in response to determining that the current position of the tracheal tube 26 is within the threshold distance of the external sensor 24, the video laryngoscope 22 provides feedback indicative of the suitable tube position at step 262. In other words, the position monitoring system 20 recognizes that, based on the position of the radiopaque markers 40, the tracheal tube 26 is proximate the external sensor 24 and therefore positioned at a desired location within the airway. The balloon cuff 30 may then be inflated to retain the tracheal tube 26 in the suitable position. It should be understood that the method 250 may be utilized to efficiently replace a first tracheal tube 26 with a second tracheal tube 26, such that the second tracheal tube 26 is disposed in substantially a same position as the first tracheal tube 26. Moreover, as discussed below, the position monitoring system 20 may be utilized to efficiently monitor the positioning of the tracheal tube 26 during the duration of the intubation, providing significant improvements over traditional x-raying procedures that intermittently verify tube placement.

Figure 9:
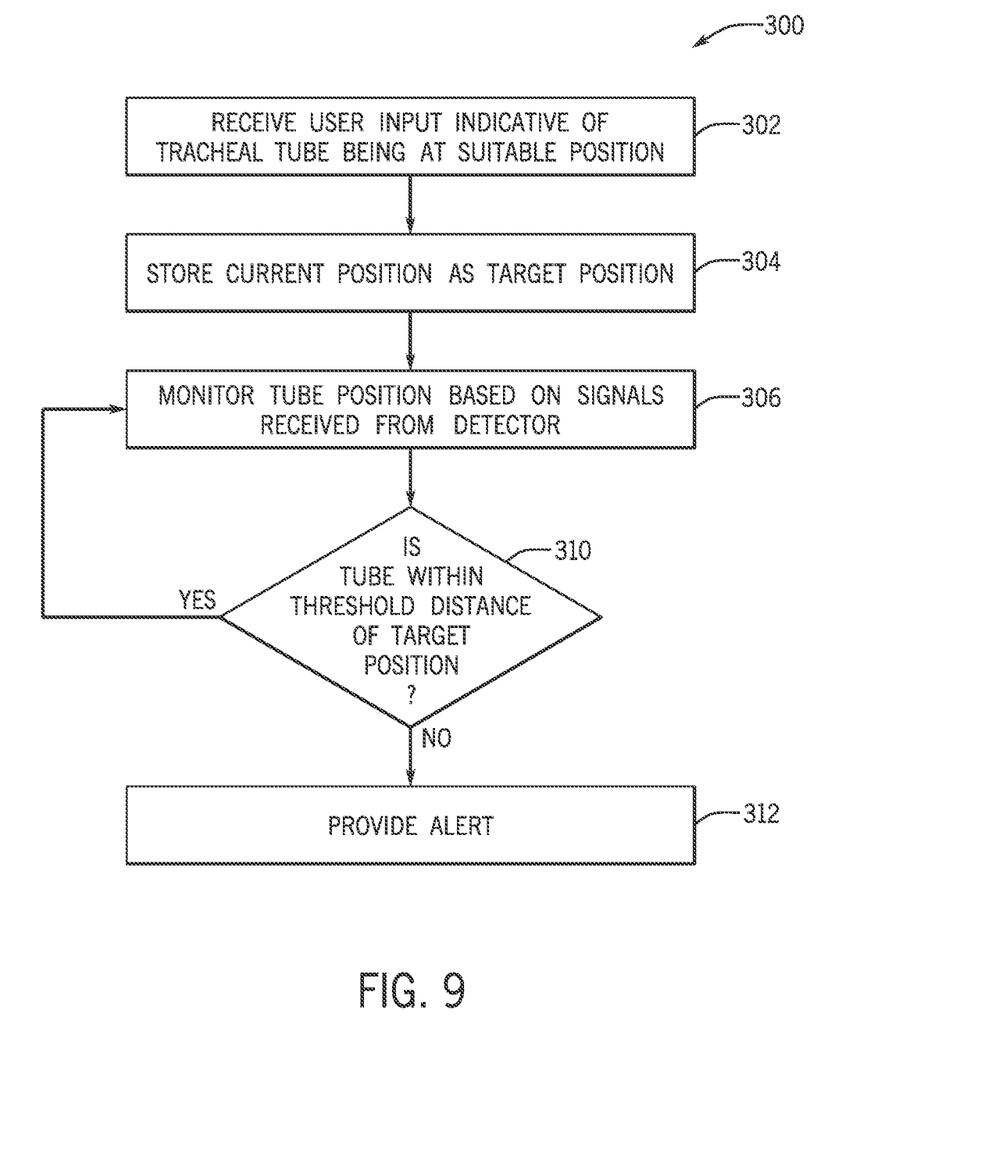
FIG. 9 is a flow diagram of a method of operating the external sensor of the position monitoring system to provide continuous tube monitoring, in accordance with certain embodiments of the present disclosure.

FIG. 9 is a flow diagram of a method 300 of operating the position monitoring system 20 to monitor intubation of a patient over a period of time, in accordance with some embodiments. The method is generally indicated by reference number 300 and includes various steps or actions represented by blocks. In an embodiment, the method 300 may be performed after the method 250 to ensure the tracheal tube 26 remains in the suitable position for the duration of intubation of the patient. Although generally discussed with reference to the external sensor 24 performing the steps of the method 300, it should be understood that certain steps or every step of the method 300 may be performed by the video laryngoscope 22 or another suitable device designed to display information to practitioners.

In the illustrated embodiment, the method 300 begins with the external sensor 24 receiving, at step 302, user input indicative of the tracheal tube 26 being at a target position within the airway. For example, as discussed above, the tracheal tube 26 may be in the target position when within a threshold distance from the external sensor 24. In some embodiments, the external sensor 24 receives the user input based on user actuation of the user-selectable button 84 of the external sensor 24 or the user-selectable button 108 of the video laryngoscope 22. That is, the position setting of the target position may be based on user experience, and may or may not be guided by laryngoscope-assisted intubation. Then, at step 304, the external sensor 24 stores the current position of the tracheal tube 26 as the target position. That is, the detector signal acquired at the time of receiving the user input indicative of the target position is stored as a calibration or a characteristic signal indicative of the target position. The external sensor 24 may therefore leverage the current position to facilitate appropriate long-term retention of the tracheal tube 26 at the target position within the airway. In certain embodiments, the external sensor 24 may pass the calibration information to the video laryngoscope 22.

It is presently recognized that in other embodiments, the external sensor 24 may operate as a primary control device, which is stand-alone relative to the video laryngoscope 22. For example, after the tracheal tube 26 is installed in the airway, the external sensor 24 may determine that the video laryngoscope 22 is powered off, decoupled from the external sensor 24, or moved outside a communication range or threshold distance from the external sensor 24. In response to the determination, the external sensor 24 may passively store the current position of the tracheal tube 26 as the target position to facilitate tube monitoring, without the video laryngoscope 22 or user actuation. Both active storage and passive storage of the target position may permit the video laryngoscope 22 to be efficiently used for intubation of multiple patients, which are each individually monitored by respective, stand-alone external sensors 24.

Continuing with the illustrated embodiment of the method 300, the external sensor 24 may monitor an updated position of the tracheal tube 26 based on updated signals received from the detector 80 at step 306. That is, as the detector 80 receives a reflected portion of the energy 56 that was released by the emitter 54, the processor 88 of the external sensor 24 may receive and analyze the updated signals from the detector 80 to determine the updated current position of the tracheal tube 26. At step 310, the external sensor 24 determines whether the updated position is within a threshold distance from the target position. It should be understood that the threshold distance is set to any suitable number corresponding to an acceptable amount of migration of the tracheal tube 26. For example, the threshold distance may be set as 1 cm, 2 cm, 3 cm, and so forth. In certain embodiments, the threshold distance may be set relative to anatomical features of the patient, such that the current position of the tracheal tube 26 is within the threshold distance if the tracheal tube 26 is positioned between the vocal cords and the carina of the patient.

In response to determining that the updated current position is within the threshold distance of the target position, the external sensor 24 determines that the tracheal tube 26 remains suitably positioned, and returns to step 306 to continue monitoring the tracheal tube 26. Alternatively, in response to determining that the current position is not within the threshold distance of the target position, the external sensor 24 may, at step 312, provide an alert or instructions indicative of the migration of the tracheal tube 26. The alert provided by the external sensor 24 may include any suitable audible or visible indication of the movement of the tracheal tube 26. For example, the external sensor 24 may instruct a speaker output device 86 to output an alarm and/or instruct a light indicator output device 86 to illuminate or flash red. In some embodiments, the external sensor 24 may instruct an external display device, a reader, or a dedicated mobile application of a smart phone or mobile device to display recommended movements to reposition the tracheal tube 26 within the threshold distance of the target position, and so forth. Via the method 300, the position monitoring system 20 may therefore effectively provide control features that facilitate the long-term installation of the tracheal tube 26.

While the present techniques are discussed in the context of endotracheal intubation, it should be understood that the disclosed techniques may also be useful in other types of airway management or clinical procedures. For example, the disclosed techniques may be used in conjunction with secretion removal from an airway, arthroscopic surgery, bronchial visualization (bronchoscopy), tube exchange, lung biopsy, nasal or nasotracheal intubation, etc. In certain embodiments, the disclosed multifunctional visualization instruments may be used for visualization of anatomy (stomach, esophagus, upper and lower airway, ear-nose-throat, vocal cords), or biopsy of tumors, masses or tissues. The disclosed multifunctional visualization instruments may also be used for or in conjunction with suctioning, drug delivery, ablation, or other treatments of visualized tissue. The disclosed multifunctional visualization instruments may also be used in conjunction with endoscopes, bougies, introducers, scopes, or probes.

The position monitoring system provided herein may be used during an endotracheal intubation to facilitate efficient placement of a tracheal tube within an airway of a patient. In particular, radiopaque markers are embedded within or disposed on a main body of the tracheal tube, which permits a detector of an external sensor to resolve a position of the tracheal tube within the airway. By positioning the external sensor on the neck of the patient at a position at which it would be desirable to dispose the tracheal tube, the position monitoring system may guide a practitioner during initial installment of the tracheal tube. For example, a display of a video laryngoscope used for the intubation may display various user interfaces that deliver information regarding suitable placement of the tracheal tube, including suggested movements. The position monitoring system may also be used to maintain the appropriate placement of the tracheal tube within the airway. For example, the position monitoring system may store a current position of the tracheal tube as a target position in response to receiving user input or determining that the video laryngoscope is decoupled from the external sensor. Then, the external sensor may determine whether the tracheal tube moves more than a specified amount from the target position and transmit alerts to instigate appropriate control actions, such as guided tube repositioning.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A position monitoring system, comprising:
a tracheal tube comprising a distal portion having one or more radiopaque indicators that change in at least one of size, shape, or density along a length of the tracheal tube, wherein the tracheal tube is configured to be positioned within an airway of a patient;
an external sensor configured to be positioned on an external surface of the patient, wherein the external sensor comprises:
an emitter that transmits energy into the neck of the patient and toward the distal portion of the tracheal tube; and
a detector that receives a portion of the transmitted energy reflected from the radiopaque indicator to permit identification of a position of the distal portion of the tracheal tube based on the change in the at least one of the size, shape, or density of the one or more radiopaque indicators; and a video laryngoscope communicatively coupled to the external sensor, wherein the video laryngoscope comprises:
a camera;
a display; and
a processor configured to:
instruct the display to present an image captured from the camera concurrently with an indication of the position of the distal portion based on feedback from the detector.

2. The position monitoring system of claim 1, wherein the processor is configured to:
receive a signal indicative of the position of the distal portion from the detector;
determine whether the position of the distal portion is within a threshold range of a target position within the airway of the patient; and
in response to determining that the position of the distal portion is within the threshold range, instruct the display to present the indication of the position of the distal portion as being within the threshold range.

3. The position monitoring system of claim 2, wherein the video laryngoscope comprises a user-selectable button, and wherein the processor of the video laryngoscope is configured to store a current position of the distal portion as the target position in response to determining the user-selectable button is actuated.

4. The position monitoring system of claim 2, wherein the video laryngoscope comprises a memory storing a plurality of target positions associated with a plurality of patient characteristics, and wherein the processor is configured to determine the target position of the distal portion by retrieving the target position from the memory based on patient characteristics.

5. The position monitoring system of claim 1, wherein the external sensor comprises a sensor processor communicatively coupled to the emitter and the detector, and wherein the sensor processor is configured to:
receive a signal indicative of the position of the distal portion from the detector;
determine whether the position of the distal portion is within a threshold range of a target position based on the signal; and
in response to determining that the position of the distal portion is within the threshold range, instruct the display of the video laryngoscope to present the indication of the position of the distal portion as being within the threshold range.

6. The position monitoring system of claim 5, wherein the external sensor comprises a user-selectable button, and wherein the sensor processor is configured to store a current position of the distal portion as the target position in response to determining the user-selectable button is actuated.

7. The position monitoring system of claim 5, wherein the external sensor comprises an output device that provides a first indication that the distal portion is within a threshold deviation from the target position and a second indication that the distal portion is outside of the threshold deviation from the target position.

8. The position monitoring system of claim 1, wherein the one or more radiopaque indicators comprise a radio-frequency identification (RFID) tag embedded in or disposed on a main body of the tracheal tube.

9. The position monitoring system of claim 1, wherein the transmitted energy is electromagnetic energy.

10. The position monitoring system of claim 1, wherein the transmitted energy is one of radio-frequency electromagnetic energy, x-ray energy, or gamma radiation energy.

11. A method, comprising:
receiving, at a video laryngoscope, communication that an external sensor is communicatively coupled;
activating functionality associated with the external sensor based on the coupling of the external sensor;
instructing, via the video laryngoscope, an emitter of an external sensor positioned on an external surface of a patient to transmit energy toward an airway of the patient;
receiving, via the video laryngoscope, a signal indicative of reflections of the transmitted energy from radiopaque indicators of a tracheal tube within the airway from a detector of the external sensor;
receiving, via the video laryngoscope, a user input that the current position of the tracheal tube is a target position;
communicating, from the video laryngoscope to the external sensor, that the tracheal tube is in the target position to cause the external sensor to store the signal indicative of detection as the target position; and
receiving, via the video laryngoscope, a confirmation of the storing from the external sensor.

12. The method of claim 11, further comprising:
receiving an indication of uncoupling of the video laryngoscope from the external sensor; and
in response to the uncoupling, storing a current position of the tracheal tube as the target position.

13. The method of claim 11, comprising:
receiving, via the video laryngoscope, an updated signal indicative of an updated position of the tracheal tube within the airway from the detector of the external sensor; and
determining, via the video laryngoscope, that the updated position deviates from the target position; and
displaying, via the video laryngoscope, an indication that the updated position deviates from the target position.

* * * * *